United States Patent [19]

Mirkovitch

[11] 4,342,745

[45] Aug. 3, 1982

[54] USE OF POLYVINYL ALCOHOLS FOR THE TREATMENT OF LESIONS

[75] Inventor: Velimir Mirkovitch, Pully, Switzerland

[73] Assignee: Zyma S.A., Nyon, Switzerland

[21] Appl. No.: 151,083

[22] Filed: May 19, 1980

[30] Foreign Application Priority Data

May 31, 1979 [CH] Switzerland ........................ 5089/79

[51] Int. Cl.$^3$ ............................................. A61K 31/74
[52] U.S. Cl. ..................................................... 424/78
[58] Field of Search ......................................... 424/78

[56] References Cited

U.S. PATENT DOCUMENTS

| | | | |
|---|---|---|---|
| 2,155,658 | 3/1939 | Herrmann et al. | 424/78 |
| 2,160,503 | 5/1939 | Herrmann | 424/78 |
| 2,693,438 | 11/1954 | Ward | 424/28 |
| 3,339,546 | 9/1967 | Chen | 128/156 |
| 3,812,252 | 5/1974 | Silvetti | 424/180 |
| 4,225,580 | 9/1980 | Rothman et al. | 424/78 |

OTHER PUBLICATIONS

Ward et al.; J. Soc. Cos. Chem., 15, 327–335, (1964).

*Primary Examiner*—Leonard Schenkman
*Attorney, Agent, or Firm*—Michael W. Glynn

[57] ABSTRACT

The subject of the present invention is the use of a polyvinyl alcohol, that is insoluble in cold water, in the form of a powder or granulate for the treatment of lesions and especially a method of treating lesions.

5 Claims, No Drawings

USE OF POLYVINYL ALCOHOLS FOR THE TREATMENT OF LESIONS

The subject of the present invention is the use of a polyvinyl alcohol, that is insoluble in cold water, in the form of a powder or granulate for the treatment of lesions and especially a method of treating lesions.

It is known that the cicatrisation of lesions of all types can be accelerated by agents having a drying and cleaning effect.

It is also known that gels and films of polyvinyl alcohols of different molecular weights have been used in the form of bandages for lesions as carriers for medicaments.

It has been found that polyvinyl alcohols, that are insoluble in cold water and that are in the form of powders or granulates, themselves have a cicatrising action. The present invention therefore relates to the use of polyvinyl alcohols, that are insoluble in cold water, in the form of powders or granulates for the treatment of lesions.

The polyvinyl alcohols that may be used according to the invention are solid, have a high degree of fluidity, are hygroscopic and are insoluble in cold water (temperature less than 20° C., and even up to 50° C.), but in boiling water their solubility is less than 12 to 13%. A polyvinyl alcohol is preferably used that has a degree of hydrolysis greater than 99.0%, such as sold, for example, under the trade name ELVANOL, type 71-30, HV, 90-50 or 85-60.

These polyvinyl alcohols are used in the form of powders or granulates, especially in the form of granulates the granules of which have an average diameter of 0.05 to 0.4 millimeters. The granules preferably have an average diameter of 0.1 to 0.2 millimeters and especially of 0.15 millimeters.

The polyvinyl alcohols have a slight disinfecting action. To increase this action it is possible to add, for use according to the invention, disinfectants used to disinfect the skin and lesions, or antibiotics, such as, for example, neomycin or Merfen (registered trade mark).

Lesions that can be treated in human and veterinary medicine with these polyvinyl alcohols are, for example, varicose ulcers, burns, especially of the 2nd and 3rd degree, post-traumatic lesions, especially if they are infected, post-operative lesions, fresh and/or infected, decubital ulcers, and, in dermatology, infected skin (pyodermia and/or mycoses) and eczemas.

The present invention also consists in a new method of treating lesions with these polyvinyl alcohols which are insoluble in cold water. It consists in covering a lesion with these polyvinyl alcohols in the form of powders or granulates and, after a certain period, preferably after 12 to 24 hours, removing the scab that has formed and covering the lesion again with these polyvinyl alcohols, this operation being repeated for at least 2 to 3 days.

The lesion is dried and cleaned by the said treatment and cicatrisation takes place substantially faster than in the case of an untreated lesion or a lesion treated with known agents. Thus it was observed that, in the case of rats (female, Wistar) and dogs (mongrels) having lesions inflicted for experimental purposes and having been treated in the manner described, i.e. the lesion was covered with the polyvinyl alcohols, the scab formed was removed after one day, the lesion was covered again with the said polyvinyl alcohols and the scab formed was removed after one day and this treatment was repeated, cicatrisation was very pronounced after treatment lasting 3 days and, by comparison with analogous untreated lesions, final cicatrisation takes place at least 2 days earlier.

The clinical results known to date shown that lesions of different aetiology react favourably to polyvinyl alcohols and to the treatment described above. In the case of a 60-year-old patient, one of whose legs had been amputated, the lesion did not respond to various other treatments over the course of 3 months. After treatment lasting 3 days with a polyvinyl alcohol, that is insoluble in cold water, in the form of a granulate the lesion was completely cicatrised and the patient was able to start using his prosthesis.

In the case of an 80-year-old female patient who had been suffering from a varicose ulcer for 20 years the polyvinyl alcohol used in the form of a powder and a granulate led to the healing of the ulcer after treatment lasting 2 weeks.

The invention also relates to polyvinyl alcohols, that are insoluble in cold water, in the form of powders or granulates, optionally together with disinfectants and/or antibiotics, as medicaments for the treatment of lesions.

I claim:

1. A method of treating a lesion selected from the group consisting of varicose ulcers, burns, post-traumatic lesions, post operative lesions, fresh decubital ulcers, infected decubital ulcers, infected skin and eczemas, which comprises topically applying to said lesion an effective amount, to cicatrise said lesion, of polyvinyl alcohol in the form of powders or granulates and which is insoluble in cold water and having a degree of hydrolysis greater than 99.0%.

2. A method of claim 1, wherein the granulates have an average granule diameter of 0.05 to 0.4 millimeters.

3. A method of claim 2, wherein the granulates have an average granule diameter of 0.1 to 0.2 millimeters.

4. A method of claim 3, wherein the granulates have an average granule diameter of 0.15 millimeters.

5. A method of one of claims 2 to 4 or 1, wherein disinfectants and/or antibiotics are added to the polyvinyl alcohol.

* * * * *